(12) United States Patent
Soo et al.

(10) Patent No.: US 10,279,010 B2
(45) Date of Patent: May 7, 2019

(54) METHODS AND COMPOSITIONS FOR MODULATING MYOFIBROBLAST ACTIVITIES

(71) Applicant: THE REGENTS OF THE UNIVERSITY OF CALIFORNIA, Oakland, CA (US)

(72) Inventors: B. Chia Soo, Beverly Hills, CA (US); Kang Ting, Beverly Hills, CA (US); Zhong Zheng, Van Nuys, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/673,880

(22) Filed: Aug. 10, 2017

(65) Prior Publication Data

US 2017/0333528 A1 Nov. 23, 2017

Related U.S. Application Data

(60) Division of application No. 14/106,617, filed on Dec. 13, 2013, now Pat. No. 9,744,214, which is a continuation of application No. PCT/US2012/042517, filed on Jun. 14, 2012.

(60) Provisional application No. 61/497,397, filed on Jun. 15, 2011.

(51) Int. Cl.
*A61K 38/18* (2006.01)
*A61K 38/17* (2006.01)

(52) U.S. Cl.
CPC .......... *A61K 38/1841* (2013.01); *A61K 38/17* (2013.01); *A61K 38/1709* (2013.01)

(58) Field of Classification Search
CPC ............ A61K 2300/00; A61K 38/1841; A61K 31/22; A61K 31/366; A61K 31/40; A61K 31/4418; A61K 31/47; A61K 31/505; A61K 31/404; A61K 31/722; A61K 35/38; A61K 35/34; A61K 45/06; A61K 31/165; A61K 35/12; A61K 35/36; A61K 38/1709; A61K 31/4174; A61K 31/43; A61K 31/65; A61K 31/7048; A61K 31/7056; A61K 35/28; A61K 38/14; A61K 48/00; A61K 9/0019; A61K 38/00; A61K 38/17; A61K 31/138; A61K 31/166; A61K 31/167; A61K 31/216; A61K 31/405; A61K 31/4166; A61K 31/439; A61K 31/44; A61K 31/4402; A61K 31/4458; A61K 31/5377; A61K 31/5415; A61K 35/22; A61K 35/407; A61K 35/50; A61K 38/1825; A61K 38/202; A61K 38/2026; A61K 38/2066; A61K 38/2086; A61K 38/2093; A61K 38/217; A61K 38/48; A61K 9/0012; A61K 2039/545; A61K 38/1816; A61K 38/193; A61K 47/30; A61K 9/0014; A61K 9/0024; A61K 9/127; A61K 9/1277; A61L 27/3633; A61L 27/54; A61L 2430/20; A61L 27/3683; A61L 2300/236; A61L 2300/41; A61L 2300/422; A61L 2300/64; A61L 2400/06; A61L 27/00; A61L 27/3637; A61L 27/367; A61L 27/3839; A61L 27/3873; A61L 27/56; A61L 27/58; A61L 2300/252; A61L 2300/622; A61L 2300/624; A61L 27/3834; A61L 17/005; A61L 17/145; A61L 2300/25; A61L 2300/258; A61L 2300/412; A61L 2300/62
See application file for complete search history.

(56) References Cited

U.S. PATENT DOCUMENTS

| 9,744,214 | B2 | 8/2017 | Soo | |
|---|---|---|---|---|
| 2008/0152639 | A1 | 6/2008 | Soo | |
| 2009/0082856 | A1* | 3/2009 | Flanagan | A61L 31/10 623/1.49 |
| 2011/0086807 | A1* | 4/2011 | Soo | A61K 31/728 514/20.8 |
| 2014/0105939 | A1 | 4/2014 | Soo | |

FOREIGN PATENT DOCUMENTS

| WO | 2010/138637 A2 | 12/2010 | | |
|---|---|---|---|---|
| WO | WO2010/138637 A2 * | 12/2010 | ........... | C07K 14/435 |
| WO | 2012174280 | 12/2012 | | |

OTHER PUBLICATIONS

Written Opinion of the International Searching Authority for International Application No. PCT/US2012/042517 dated Feb. 1, 2013.
International Search Report of the International Searching Authority for International Application No. PCT/US2012/042517 dated Feb. 1, 2013.
International Preliminary Report on Patentability for International Application No. PCT/US2012/042517 dated Dec. 17, 2013.
Andriamanalijaona, R. et al. "Effect of Interleukin-1 beta on Transforming Growth Factor-Beta and Bone Morphobenic Protein-2 Expression in Human Periodontal Ligament and Alveolar Bone Cells in Culture: Modulation by Avocado and Soybean Unsaponifiables", vol. 77, No. 7, J. Periodontol, Jul. 2006, pp. 1156-1166.
Soo, B. Chia; Advisory Action for U.S. Appl. No. 14/106,617, filed Dec. 13, 2013, dated Sep. 20, 2016, 3 pgs.

(Continued)

*Primary Examiner* — Audrea B Coniglio
(74) *Attorney, Agent, or Firm* — Taylor English Duma LLP

(57) ABSTRACT

The present invention discloses methods and compositions for treating or ameliorating a condition associated with increased or decreased myofibroblast activities and use thereof.

5 Claims, 6 Drawing Sheets

(56) References Cited

OTHER PUBLICATIONS

Soo, B. Chia; Applicant Interview Summary for U.S. Appl. No. 14/106,617, filed Dec. 13, 2013, dated Jan. 22, 2016, 3 pgs.
Soo, B. Chia; Final Office Action for U.S. Appl. No. 14/106,617, filed Dec. 13, 2013, dated May 23, 2016, 13 pgs.
Soo, B. Chia; Issue Notification for U.S. Appl. No. 14/106,617, filed Dec. 13, 2013, dated Aug. 9, 2017, 1 pg.
Soo, B. Chia; Non-Final Office Action for U.S. Appl. No. 14/106,617, filed Dec. 13, 2013, dated Oct. 20, 2016, 9 pgs.
Soo, B. Chia; Non-Final Office Action for U.S. Appl. No. 14/106,617, filed Dec. 13, 2013, dated Oct. 22, 2015, 10 pgs.
Soo, B. Chia; Notice of Allowance for U.S. Appl. No. 14/106,617, filed Dec. 13, 2013, dated Apr. 26, 2017, 8 pgs.
Soo, B. Chia; Restriction Requirement for U.S. Appl. No. 14/106,617, filed Dec. 13, 2013, dated May 12, 2015, 9 pgs.

\* cited by examiner

METHODS AND COMPOSITIONS FOR MODULATING MYOFIBROBLAST ACTIVITIES

This application is a divisional application of pending U.S. patent application Ser. No. 14/106,617 filed Dec. 13, 2013, which in turn is a continuation application of International Application No. PCT/US2012/042517 filed Jun. 14, 2012, which in turn claims the benefit of U.S. Provisional Patent Application No. 61/497,397 filed Jun. 15, 2011, all of which are hereby incorporated by reference herein in their entirety.

FIELD OF THE INVENTION

The present invention generally relates to methods and compositions for treating or ameliorating a condition associated with increased or decreased myofibroblast activities and use thereof.

BACKGROUND OF THE INVENTION

Excessive or deficient myofibroblast activity is associated with many diseases and biological and medical processes. Such diseases include those shown in Table 1*.

| Tissue or Organ | Activation/Proliferation | Deletion or Damage |
|---|---|---|
| Skin | | |
| Granulation tissue | Scleroderma; keloid; Dupuytren's contracture (72, 213, 224); psoriasis (63) | |
| Pericyte | Atherosclerosis and restenosis (149, 159); hypertension (208) | Microaneurysms, edema, and hemorrhage (26, 239) |
| Mouth | | |
| Periodontal ligament Gingival myofibroblasts | Periodontal disease (136, 214) Gingival hypertrophy secondary to drugs (cyclosporine and Dilantin) (135, 136, 212, 214, 216) | |
| Eye Orbital fibroblast Retinal myofibroblast Anterior capsule of lens Corneal myofibroblast Heart and pericardium | Exophthalmos (proptosis) of Grave's disease (9, 221, 254) Proliferative vitreoretinopathy (253) Anterior capsular cataract (172, 217) Corneal scarring (184) Myocardial fibrosis, atherosclerosis, and coronary artery restenosis (35, 149, 159. 258) | Diabetic microaneurysm (26, 142, 239) |
| Kidney | | |
| Mesangial cell | Proliferative and sclerosing glomerulonephritis (108, 184, 239) | Absence of glomerular structure (141, 234) |
| Interstitial cell | Renal tubulointerstitial fibrosis (171, 177, 198, 239) | |
| Liver | | |
| Perisinusoidal stellate (Ito cell) | Fibrosis and cirrhosis (72, 88, 150) Ischemia reperfusion injury of hepatic transplantation (206) Necrotizing hepatitis (62) | |
| Pancreas | | |
| Periacinal stellate cell | Pancreatic fibrosis (4, 8) | |
| Lung | | |
| Interstitial contractile cell | Pulmonary interstitial fibrosis, idiopathic and drug-induced; sarcoidosis (105, 209, 214) | Emphysema (25) |
| Stomach and intestine Interstitial cell of Cajal Subepithelial myofibroblast | Collagenous colitis; villous atrophy and crypt hyperplasia; fibrosis of Crohn's disease (2, 86, 114, 131, 153) Healing gastric ulcer | Abnormal intestinal motility; hypertrophic pyloric stenosis; Hirschsprung's disease; megacolon of piebaldism; idiopathic pseudo-obstruction (33, 52, 115, 183, 212, 243, 248, 249) |
| Brain Astrocyte | Produce glial scar tissue (166) | Human immunodeficiency virus-associated cognitive motor disease; spongiform encephalopathy (166) |
| Breast | | |
| Stromal myofibroblast | Fibrocystic disease; desmoplastic reaction to breast cancer (73, 214) | |

-continued

| Tissue or Organ | Activation/Proliferation | Deletion or Damage |
|---|---|---|
| Bone marrow | | |
| Stromal myofibroblast | Fibrosis in myelodysplasia and neoplastic diseases (182, 218) | Aplastic anemia (182, 218) |
| Joint | | |
| Synoviocyte | Rheumatoid pannus formation (11) | |

*See Table 5 of Powell, et al., Myofibroblasts. I. Paracrine cells important in health and disease, Am J Physiol Cell Physiol Jul. 1, 1999 vol. 277 no. 1 C1-C19, references shown in this table refers to the articles cited in Powell, et al.

Thus far, there are no effective ways of treating or ameliorating many of the conditions associated with excessive or deficient myofibroblast activities.

Therefore, there is a need for methods and compositions for modulating myofibroblast activity.

The embodiments below address the above identified issues and needs.

SUMMARY OF THE INVENTION

In one aspect of the present invention, it is provided method for treating or ameliorating a disorder associated with increased or decreased myofibroblast activity, which method comprising modulating the myofibroblast level in a subject in need thereof by modulating fibromodulin level in the subject. The subject can be a mammal, e.g., a patient or an animal.

In some embodiments of the method, modulating myofibroblast level comprises increasing fibromodulin level.

In some embodiments of the method, modulating myofibroblast level comprises decreasing fibromodulin level.

In some embodiments of the method, modulating fibromodulin level in the subject comprises effectively modulating the level of fibromodulin activity so as to modulate activities of a myofibroblast apoptosis inducing agent. Such myofibroblast apoptosis inducing agent can be, e.g., interleukin-1β (IL-1β).

In some embodiments of the method, modulating myofibroblast level comprises applying to the subject an effective amount of fibromodulin for promoting myofibroblast differentiation and apoptosis thereby increasing the myofibroblast level in the subject where early, but short duration myofibroblast activity is effective for the disorder or inhibiting prolonged myofibroblast activity in the subject where the disorder is associated with prolonged myofibroblast activity, wherein the myofibroblast differentiation is induced by a myofibroblast inducing agent.

In some embodiments of the method, modulating myofibroblast level comprises blocking fibromodulin activity so as to prolong myofibroblast activity.

In some embodiments of the method, blocking fibromodulin activity comprises administering to the subject anti-sense oligonucleotides, antibodies, peptides that inhibit fibromodulin activities, and combinations thereof.

In some embodiments of the method, the disorder is atherosclerosis, restenosis, cirrhosis, hemorrhage, microaneurysms, wounds with impaired cell motility, diabetic wounds, wounds with impaired tensile strength, wounds in patients on corticosteroids, wounds in olders, emphysema, interstitial lung diseases, asthma, Dupuytren's contracture, or another disease in Table 1.

In some embodiments of the method, optionally in combination with any or all of the above embodiments, the myofibroblast differentiation inducing agent is TGF-β1.

In another aspect of the present invention, it is provided a composition, which composition comprising an effective amount of fibromodulin for promoting myofibroblast differentiation and apoptosis in a subject having a disorder associated with myofibroblast activity.

In some embodiments of the composition, the composition further comprises an excipient (e.g., a polymer or a formulation carrier described below), wherein the formulation is a formulation for topical, transdermal, intradermal, or microneedle delivery.

In some embodiments of the composition, optionally in combination with any or all the above embodiments, the composition is included in a medical device comprising the composition.

In some embodiments, the medical device is a stent.

In a further aspect of the present invention, it is provided a method of forming a medical device, comprising applying a composition of the various above embodiments to the medical device. Such applying can be, e.g., forming a coating comprising the composition on the surface of the medical device. In some embodiments, the medical device is a stent.

DETAILED DESCRIPTION OF THE INVENTION

Figure 1:
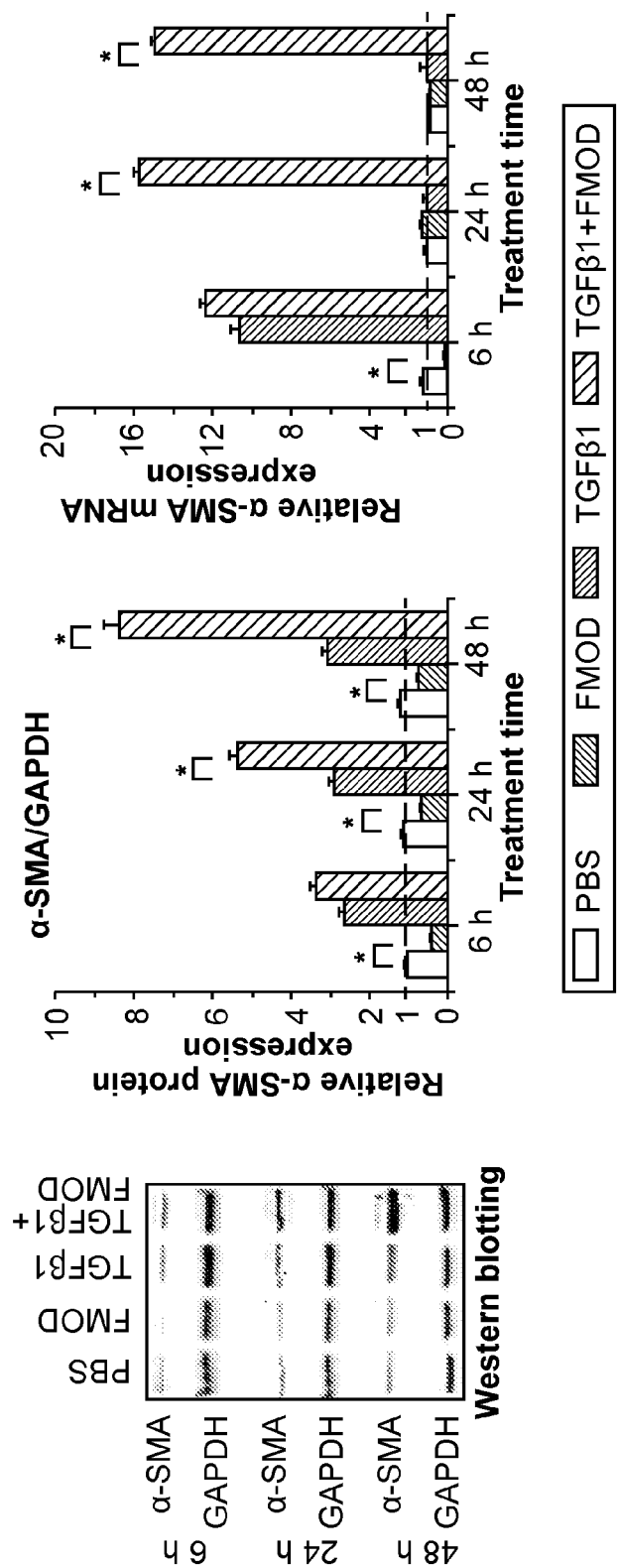
FIG. 1 summarizes results of western blotting and quantitative RT-PCR (qRT-PCR) analyses which revealed that fibromodulin (FMOD) alone had no significant effect on rat dermal fibroblast (RDF) α-smooth muscle actin (α-SMA) expression. However, when in the presence of TGF-β1, FMOD significantly enhances TGF-β1-induced α-SMA expression. Data are normalized to untreated RDFs at time 0 (dash lines). N=3. *, P<0.05.

In one aspect of the present invention, it is provided method for treating or ameliorating a disorder associated with increased or decreased myofibroblast activity, which method comprising modulating the myofibroblast level in a subject in need thereof by modulating fibromodulin level in the subject. The subject can be a mammal, e.g., a patient or an animal.

In some embodiments of the method, modulating myofibroblast level comprises increasing fibromodulin level. Increasing fibromodulin level can be achieved by endogenously increasing fibromodulin level via, e.g., genetic engineering using a DNA or cDNA sequence expressing fibromodulin protein or peptide. Genetic engineering technology is well established and can be readily achieved by a person of ordinary skill in the art.

In some embodiments, increasing fibromodulin level can be achieved by exogenously increasing fibromodulin level by, e.g., administering to a subject a fibromodulin protein or peptide. In some embodiments, such fibromodulin protein or peptide can be included in a composition, which can be formulated into various formulations for different modes of administration. More detailed description of such formulations is provided below.

In some embodiments of the method, modulating myofibroblast level comprises decreasing fibromodulin expression level. Decreasing fibromodulin expression level can be achieved by established method of decreasing expression level of a protein, e.g., gene knockout, gene deletion, etc. Such gene knockout or deletion methodologies are well established and can be readily carried out by a person of ordinary skill in the art. Decreasing fibromodulin level can decrease myofibroblast differentiation induced by a myofibroblast inducing agent and apoptosis so as to prolong myofibroblast activity.

In some embodiments of the method, modulating fibromodulin level in the subject comprises effectively modulating the level of fibromodulin activity so as to modulate activities of a myofibroblast apoptosis inducing agent. Such myofibroblast apoptosis inducing agent can be, e.g., interleukin-1β (IL-1β).

In some embodiments of the method, modulating myofibroblast level comprises applying to the subject an effective amount of fibromodulin for promoting myofibroblast differentiation and apoptosis thereby increasing the myofibroblast level in the subject where early, but short duration myofibroblast activity is effective for the disorder or inhibiting prolonged myofibroblast activity in the subject where the disorder is associated with prolonged myofibroblast activity, wherein the myofibroblast differentiation is induced by a myofibroblast inducing agent.

In some embodiments of the method, modulating myofibroblast level comprises blocking fibromodulin activity so as to prolong myofibroblast activity.

In some embodiments of the above methods, blocking fibromodulin activity comprises administering to the subject anti-sense oligonucleotides, antibodies, peptides that inhibit fibromodulin activities, and combinations thereof. Medical conditions can benefit from (e.g., treated or ameliorated) prolonged myofibroblast activity. A number of examples of such medical conditions or disorders are shown in Table 1.

In some embodiments of the above methods, modulating myofibroblast level comprises applying to the subject an effective amount of fibromodulin for promoting myofibroblast differentiation and apoptosis thereby increasing the myofibroblast level in the subject where early, but short duration myofibroblast activity is effective for the disorder or inhibiting prolonged myofibroblast activity in the subject where the disorder is associated with prolonged myofibroblast activity. Such disorders include, e.g., wounds with impaired cell motility such as diabetic wounds; wounds with impaired tensile strength such as wounds in patients on corticosteroids; wounds in olders; emphysema; interstitial lung diseases; asthma; Dupuytren's contracture.

In some embodiments of the method, the disorder is atherosclerosis, restenosis, cirrhosis, hemorrhage, microaneurysms, wounds with impaired cell motility, diabetic wounds, wounds with impaired tensile strength, wounds in patients on corticosteroids, wounds in olders, emphysema, interstitial lung diseases, asthma, Dupuytren's contracture, or another disease in Table 1.

In another aspect of the present invention, it is provided a composition. The composition comprises an effective amount of fibromodulin for promoting myofibroblast differentiation and apoptosis in a subject having a disorder associated with myofibroblast activity.

In some embodiments of the method, optionally in combination with any or all of the above embodiments, the myofibroblast differentiation inducing agent is TGF-β1.

In another aspect of the present invention, it is provided a composition, which composition comprising an effective amount of fibromodulin for promoting myofibroblast differentiation and apoptosis in a subject having a disorder associated with myofibroblast activity.

In some embodiments of the composition, the composition further comprises an excipient (e.g., a polymer or a formulation carrier described below), wherein the formulation is a formulation for topical, transdermal, intradermal, or microneedle delivery.

In some embodiments of the composition, optionally in combination with any or all the above embodiments, the composition is included in a medical device comprising the composition.

In some embodiments, the medical device is a stent.

In a further aspect of the present invention, it is provided a method of forming a medical device, comprising applying a composition of the various above embodiments to the medical device. Such applying can be, e.g., forming a coating comprising the composition on the surface of the medical device. In some embodiments, the medical device is a stent.

As used herein, the term "myofibroblast differentiation inducing agent" shall mean any proteineous or small molecule agent capable of inducing myofibroblast differentiation. An example of such myofibroblast differentiation inducing agents is transforming growth factor (TGF)-β1.

As used herein, the term "myofibroblast apoptosis inducing agent" shall mean any proteineous or small molecule agent capable of inducing myofibroblast apoptosis. An example of such myofibroblast apoptosis inducing agents is interleukin-1β (IL-1β).

As used herein, the term "increased myofibroblast activity" shall mean the level of myofibroblast activity exceeds the normal level myofibroblast activity in a subject (e.g., a human being), which is within the general knowledge of a medical practitioner. In some times, the term "increased myofibroblast activity" can be used interchangeably with the term "excessive myofibroblast activity."

As used herein, the term "decreased myofibroblast activity" shall mean the level of myofibroblast activity falls below the normal level myofibroblast activity in a subject (e.g., a human being), which is within the general knowledge of a medical practitioner. In some times, the term "decreased myofibroblast activity" can be used interchangeably with the term "insufficient myofibroblast activity."

Myofibroblast Activity and Fibromodulin

Figure 2:
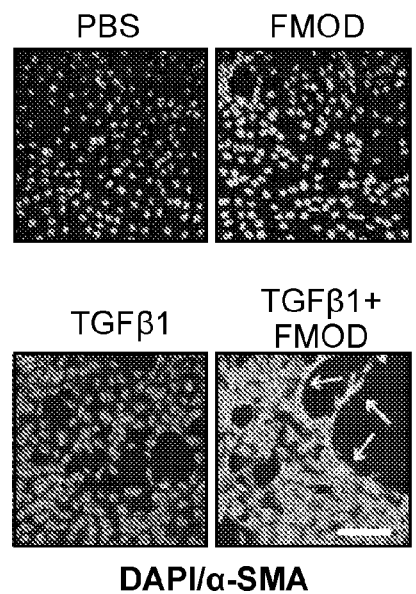
FIG. 2 shows results of an immunofluorescent (IF) staining study which revealed that FMOD, when combined with TGF-β1, significantly enhanced myofibroblast differentiation and contractility in vitro. Formation of stress fibers stained strongly for α-SMA are indicated by yellow arrows. Scale bar=100 μm.
Figure 3:
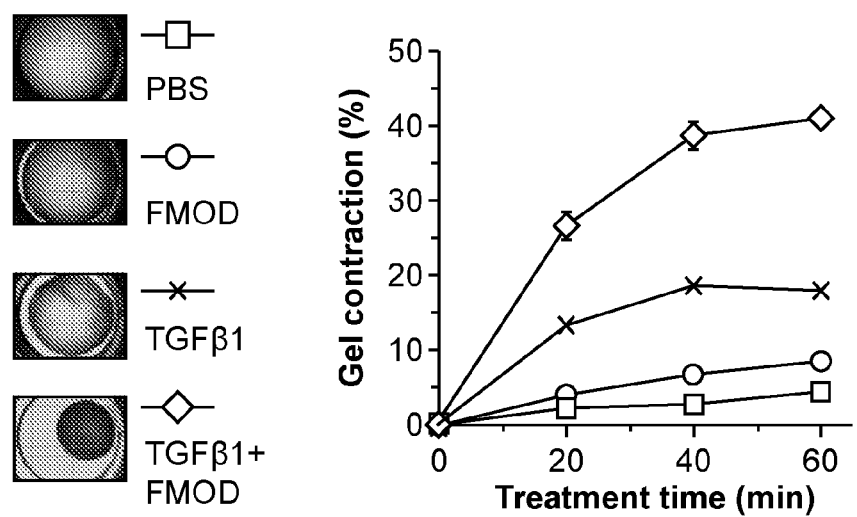
FIG. 3 shows that FMOD+TGF-β1 significantly promotes TGF-β1-mediated RDF contraction in collagen gel, while FMOD alone had minimal effects. N=6.
Figure 4:
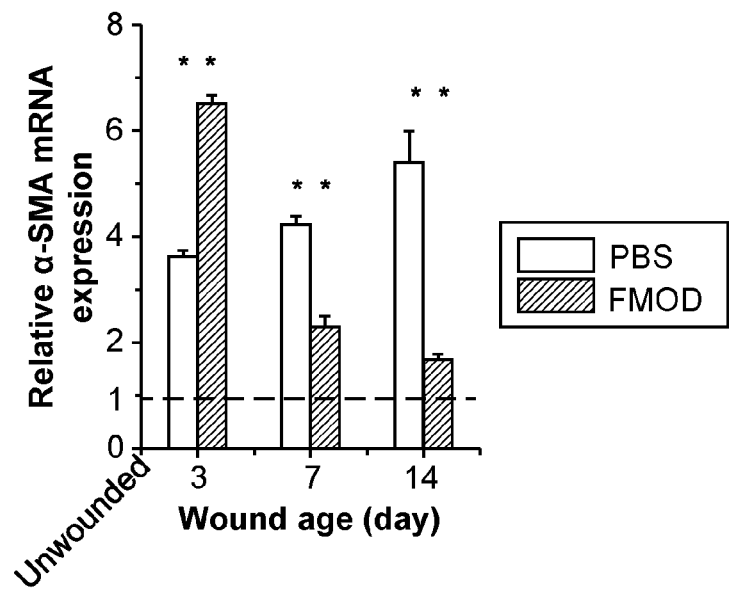
FIG. 4 shows the results of a PCR array assay which revealed that expression of α-SMA were significantly upregulated in FMOD-treated adult rat wounds at the early 3-day time-point, but reduced at the late 7- and 14-day time-points. Gene expression is normalized to unwounded skin (dashed lines). N=9 wounds from 9 animals. **, P<0.01.

Activity level of myofibroblast is related to the activity of fibromodulin. Fibromodulin can promote myofibroblast differentiation and apoptosis. Fibromodulin addition in the presence of transforming growth factor (TGF)-1β significantly promoted TGF-β1-mediated rat dermal fibroblasts (RDFs) α-smooth muscle actin (α-SMA, a wildly used myofibroblast marker) expression (FIG. 1). Remarkably, fibromodulin, when combined with TGF-β1, significantly enhanced myofibroblast differentiation and contractility in vitro (FIG. 2). Quantitative in vitro collagen gel contraction studies confirmed increased contractility of FMOD+TGF-β1 induced myofibroblasts relative to TGF-β1 alone (FIG. 3). In addition, expression of α-SMA were significantly upregulated in FMOD-treated adult rat wounds at the early 3-day time-point, but reduced at the late 7- and 14-day time-points (FIG. 4).

Figure 5:
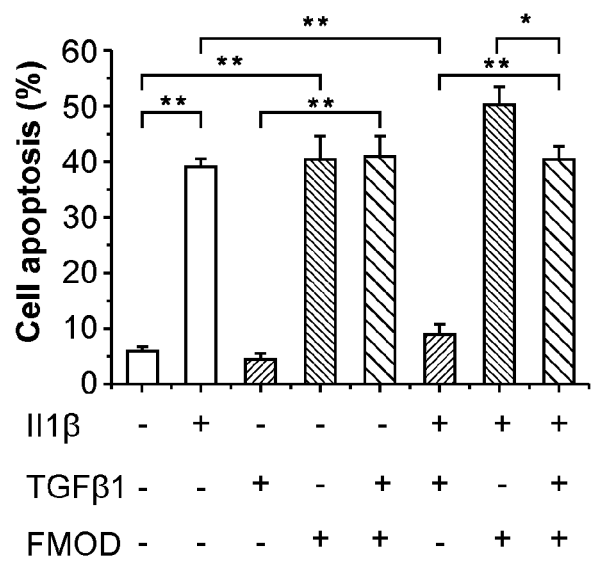
FIG. 5 shows that FMOD alone induces myofibroblast apoptosis as effectively as IL-1β, even in the presence of TGF-β1. N=6. *, P<0.05; **, P<0.01.
Figure 6:
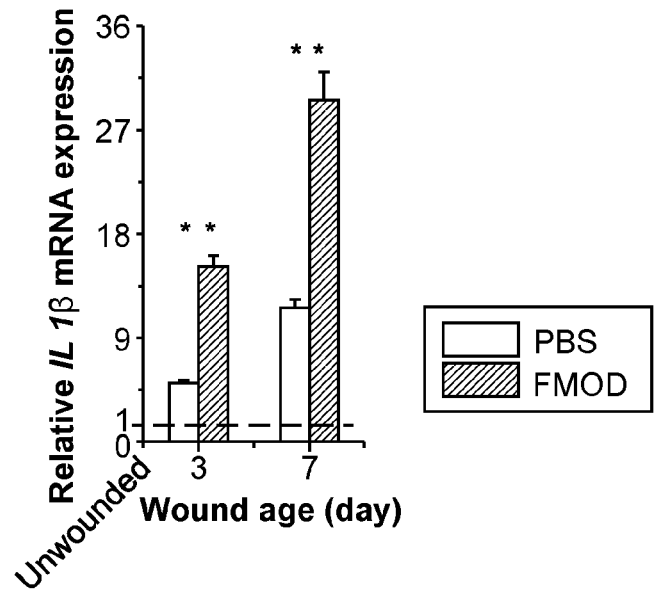
FIG. 6 shows results of PCR array assay which revealed that FMOD significantly stimulated IL-1β expression in day 3 and 7 adult rat wounds. Gene expression is normalized to unwounded skin (dashed lines). N=9 wounds from 9 animals. **, P<0.01.
Figure 7:
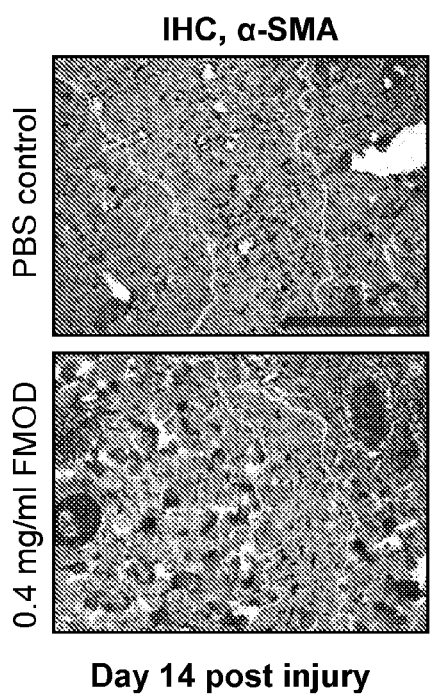
FIG. 7 shows that decreased α-SMA-positive myofibroblasts are found in FMOD-treated wounds at day 14 post injury. Scale bar=200 μm.

Notably, TGF-β1 completely blocked interleukin (IL)-β1-mediated apoptosis in myofibroblasts (FIG. 5). Surprisingly, FMOD alone promoted myofibroblast apoptosis as effectively as IL-1β, but more strikingly, FMOD administration promoted apoptosis even in the presence of TGF-1β (FIG. 5). Furthermore, FMOD significantly stimulated IL-1β expression in day 3 and 7 adult rat wounds (FIG. 6), which correlated functionally with diminished α-SMA-positive myofibroblast numbers by day 14 post injury (FIG. 7). Taken together, FMOD not only promotes TGF-β1-induced myofibroblast differentiation and contractility, but also accelerates myofibroblast clearance—resulting in lack of myofibroblast persistence in remodeling stage of FMOD-treated wounds.

As used herein, the term "fibromodulin" includes fibromodulin protein and peptides. Examples of fibromodulin protein and peptides are described in U.S. patent application Ser. No. 13/322,124, which is a national phase application of PCT/US2010/036262. Teachings in these applications are incorporated herein in their entirety by reference.

Formulation Carriers

The composition described herein may be administered to a subject in need of treatment by a variety of routes of administration, including orally and parenterally, (e.g., intravenously, subcutaneously or intramedullary), intranasally, as a suppository or using a "flash" formulation, i.e., allowing the medication to dissolve in the mouth without the need to use water, topically, intradermally, subcutaneously and/or administration via mucosal routes in liquid or solid form. The pharmaceutical composition can be formulated into a variety of dosage forms, e.g., extract, pills, tablets, microparticles, capsules, oral liquid.

There may also be included as part of the composition pharmaceutically compatible binding agents, and/or adjuvant materials. The active materials can also be mixed with other active materials including antibiotics, antifungals, other virucidals and immunostimulants which do not impair the desired action and/or supplement the desired action.

In some embodiments, the composition can be formulated into a formulation for bone, which can include a carrier such as collagen, atelocollagen (collagen treated to remove the immunogenic ends), hydroxyapatite, and a polymer, which is further described below. In these embodiments, the formulation can comprise a porous matrix or microspheres made of a polymeric material, which is further described below. In some embodiments, the polymer can be, e.g., polylactic acid or polylactide (PLA), or poly(lactic acid-co-glycolic acid), or another bioabsorbable polymer.

In one embodiment, the mode of administration of the pharmaceutical composition described herein is oral. Oral compositions generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. Some variation in dosage will necessarily occur, however, depending on the condition of the subject being treated. These preparations should produce a serum concentration of active ingredient of from about 0.01 nM to 1,000,000 nM, e.g., from about 0.2 to 40 µM. A preferred concentration range is from 0.2 to 20 µM and most preferably about 1 to 10 µM. However, the concentration of active ingredient in the drug composition itself depends on bioavailability of the drug and other factors known to those of skill in the art.

In another embodiment, the mode of administration of the pharmaceutical compositions described herein is topical or mucosal administration. A specifically preferred mode of mucosal administration is administration via female genital tract. Another preferred mode of mucosal administration is rectal administration.

Various polymeric and/or non-polymeric materials can be used as adjuvants for enhancing mucoadhesiveness of the pharmaceutical composition disclosed herein. The polymeric material suitable as adjuvants can be natural or synthetic polymers. Representative natural polymers include, for example, starch, chitosan, collagen, sugar, gelatin, pectin, alginate, karya gum, methylcellulose, carboxymethylcellulose, methylethylcellulose, and hydroxypropylcellulose. Representative synthetic polymers include, for example, poly(acrylic acid), tragacanth, poly(methyl vinylether-co-maleic anhydride), poly(ethylene oxide), carbopol, poly(vinyl pyrrolidine), poly(ethylene glycol), poly(vinyl alcohol), poly(hydroxyethylmethylacrylate), and polycarbophil. Other bioadhesive materials available in the art of drug formulation can also be used (see, for example, Bioadhesion—Possibilities and Future Trends, Gurny and Junginger, eds., 1990).

It is to be noted that dosage values also vary with the specific severity of the disease condition to be alleviated. It is to be further understood that for any particular subject, specific dosage regimens should be adjusted to the individual need and the professional judgment of the person administering or supervising the administration of the aforesaid compositions. It is to be further understood that the concentration ranges set forth herein are exemplary only and they do not limit the scope or practice of the invention. The active ingredient may be administered at once, or may be divided into a number of smaller doses to be administered at varying intervals of time.

The composition may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methylparabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

The composition of the present invention can be prepared as formulations with pharmaceutically acceptable carriers. Preferred are those carriers that will protect the active compound against rapid elimination from the body, such as a controlled release formulation, including implants and microencapsulated delivery systems. Biodegradable, biocompatible polymers can be used, such as polyanhydrides, polyglycolic acid, collagen, and polylactic acid. Methods for preparation of such formulations can be readily performed by one skilled in the art.

Liposomal suspensions (including liposomes targeted to infected cells with monoclonal antibodies to viral antigens) are also preferred as pharmaceutically acceptable carriers. Methods for encapsulation or incorporation of compounds into liposomes are described by Cozzani, I.; Jori, G.; Bertoloni, G.; Milanesi, C.; Sicuro, T. Chem. Biol. Interact. 53, 131-143 (1985) and by Jori, G.; Tomio, L.; Reddi, E.; Rossi, E. Br. J. Cancer 48, 307-309 (1983). These may also be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Other methods for encapsulating compounds within liposomes and targeting areas of the body are described by Sicuro, T.; Scarcelli, V.; Vigna, M. F.; Cozzani, I. Med. Biol. Environ. 15(1), 67-70 (1987) and Jori, G.; Reddi, E.; Cozzani, I.; Tomio, L. Br. J. Cancer, 53(5), 615-21 (1986).

The composition described herein may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like according to a specific dosage form.

Thus, for example, for purposes of oral administration, tablets containing various excipients such as sodium citrate, calcium carbonate and/or calcium phosphate may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

The composition described herein can be formulated alone or together with the other agent in a single dosage form or in a separate dosage form. Methods of preparing various pharmaceutical formulations with a certain amount of active ingredient are known, or will be apparent in light of this disclosure, to those skilled in this art. For examples of methods of preparing pharmaceutical formulations, see Remington's Pharmaceutical Sciences, Mack Publishing Company, Easton, Pa., 19th Edition (1995).

In some embodiments, the composition of the various embodiments disclosed above can be formulated into implants, scaffolds, patches, etc.

EXAMPLES

The embodiments of the present invention will be illustrated by the following set forth examples. All parameters and data are not to be construed to unduly limit the scope of the embodiments of the invention.

Example 1

Using fibromodulin protein and peptide to accelerate myofibroblast differentiation and apoptosis or to inhibit prolonged myofibroblast activity has been tested, and the results are positive (data not shown).

Figure 8A:
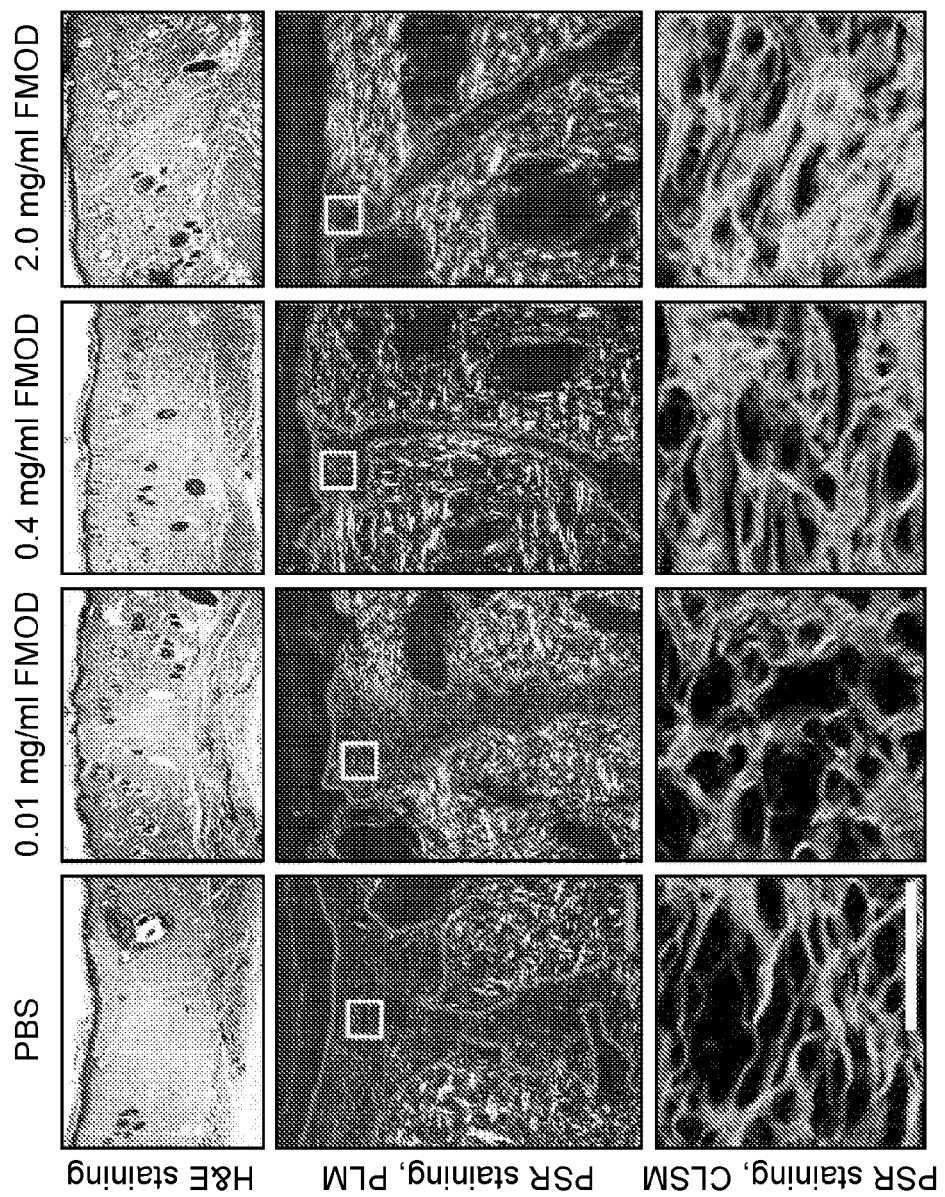
FIGS. 8A-8C show that FMOD reduces scar formation in adult rat wounds and increases tensile strength. At doses ≥0.4 mg/ml, histological (A) and quantitative analyses (B) demonstrate that FMOD significantly reduces scar size of adult rat skin wounds compared to control at day 14 post injury, while increasing tensile strength in a dose dependent manner (C). Scale bar=25 μm.
Figures 8B, 8C:
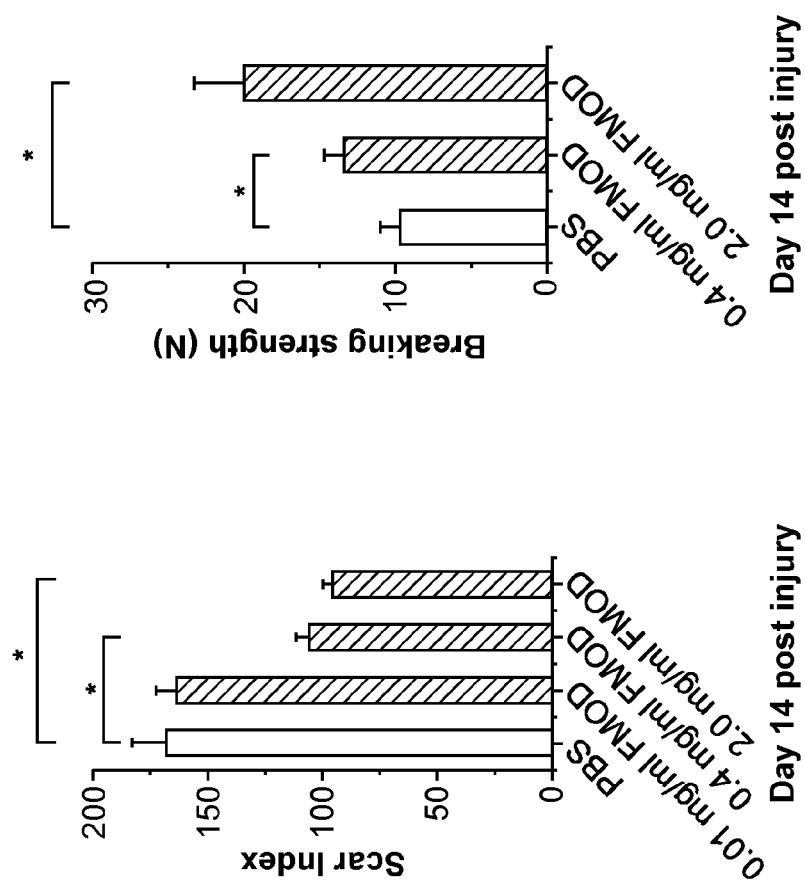

Expression of α-SMA were significantly upregulated in FMOD-treated adult rat wounds at the early 3-day time-point, but reduced at the late 7-and 14-day time-point (FIG. 4). Notably, TGF-β1 completely blocked interleukin (IL)-1β-mediated apoptosis in myofibroblasts (FIG. 5). Surprisingly, FMOD alone promoted myofibroblast apoptosis as effectively as IL-1β, but more strikingly, FMOD administration promoted apoptosis even in the presence of TGF-1β (FIG. 5). Furthermore, FMOD significantly stimulated IL-1β expression in day 3 and 7 adult rat wounds (FIG. 6), which correlated functionally with diminished α-SMA-positive myofibroblast numbers by day 14 post injury (FIG. 7). Taken together, FMOD not only promotes TGF-β1-induced myofibroblast differentiation and contractility, but also accelerates myofibroblast clearance—resulting in lack of myofibroblast persistence in remodeling stage of FMOD-treated wounds. As the result of this, FMOD treated adult rat primary closure wounds healed with significant smaller scar accompanied with more organized collagen architecture and stronger tensile strength (FIG. 8).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A method of forming a medical device, comprising applying a composition to the medical device, the composition comprising an effective amount of fibromodulin for promoting myofibroblast differentiation and apoptosis in a subject having a disorder associated with myofibroblast activity, wherein the composition is a controlled release formulation that provides controlled release of fibromodulin, and wherein the composition further comprises TGF-β1.

2. The method of claim 1, wherein the medical device is a stent.

3. The method of claim 1, wherein the composition further comprises a polymer, and wherein the composition forms a coating on the medical device.

4. A medical device comprising the composition of claim 1.

5. The medical device of claim 4, which is a stent.

* * * * *